US011642156B2

(12) United States Patent
Bennett et al.

(10) Patent No.: US 11,642,156 B2
(45) Date of Patent: May 9, 2023

(54) BONE REDUCTION INSTRUMENT, SYSTEM, AND METHOD

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Charles R. Bennett, Memphis, TN (US); Nicholas S. Ritchey, Collierville, TN (US); Nathaniel Kelley Grusin, Germantown, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 17/546,395

(22) Filed: Dec. 9, 2021

(65) Prior Publication Data

US 2022/0183730 A1 Jun. 16, 2022

Related U.S. Application Data

(60) Provisional application No. 63/126,212, filed on Dec. 16, 2020.

(51) Int. Cl.
*A61B 17/80* (2006.01)
*A61B 17/88* (2006.01)
*A61B 17/84* (2006.01)

(52) U.S. Cl.
CPC ........ *A61B 17/8019* (2013.01); *A61B 17/808* (2013.01); *A61B 17/8014* (2013.01); *A61B 17/842* (2013.01); *A61B 17/88* (2013.01)

(58) Field of Classification Search
CPC ............ A61B 17/8004; A61B 17/8019; A61B 17/808; A61B 17/88; A61B 17/885; A61B 17/8872
See application file for complete search history.

(56) References Cited

U.S. PATENT DOCUMENTS

| 3,709,219 A | * | 1/1973 | Halloran | ................ | A61B 17/60 |
| | | | | | 606/57 |
| 9,113,969 B2 | * | 8/2015 | Niederberger | ..... | A61B 17/8019 |

(Continued)

OTHER PUBLICATIONS

"MIO—Compression Plating for Simple Fractures, Transverse" by AO Foundation, [online] 2012 [retrieved on Nov. 15, 2021]. Retrieved from Internet URL: https://surgeryreference.aofoundation.org/orthopedic-trauma/adult-trauma/tibial-shaft/simple-fracture-transverse/mio-compression-plating#reduction, 20 pages.

*Primary Examiner* — Larry E Waggle, Jr.
(74) *Attorney, Agent, or Firm* — KDW Firm PLLC

(57) ABSTRACT

An orthopedic instrument for manipulating (e.g., compressing or distracting) one or more patient's bone fragments is disclosed. In one embodiment, the orthopedic instrument includes forceps having first and second arms and first and second handles, respectively. Each arm including a coupling mechanism for selectively engaging removable tips or bell housings. Each tip or bell housing including a first end arranged and configured to mate with a fastener hole or opening formed in a bone plate, a second end arranged and configured to receive a head portion of a bone fastener, and an intermediate portion arranged and configured to couple to the coupling mechanism of the first and second arms. In addition, the orthopedic instrument may include a force sensing mechanism or gauge arranged and configured to measure an amount of force being applied across the bone fracture.

25 Claims, 8 Drawing Sheets

(56) References Cited

U.S. PATENT DOCUMENTS

| | | | | |
|---|---|---|---|---|
| 9,351,773 B2* | 5/2016 | DiDomenico | ..... | A61B 17/8004 |
| 9,597,130 B2* | 3/2017 | Pappalardo | ........ | A61B 17/8866 |
| 10,285,742 B1* | 5/2019 | Patterson | ......... | A61B 17/8019 |
| 2011/0264149 A1 | 10/2011 | Pappalardo et al. | | |

* cited by examiner

BONE REDUCTION INSTRUMENT, SYSTEM, AND METHOD

CROSS-REFERENCE TO RELATED APPLICATIONS

This is a non-provisional of, and claims the benefit of the filing date of, pending U.S. provisional patent application No. 63/126,212, filed Dec. 16, 2020, entitled "Bone Plate Reduction Instrument", the entirety of which application is incorporated by reference herein.

FIELD OF THE INVENTION

The present disclosure is directed to orthopedic instrumentation and more specifically, to an orthopedic device, instrument, tool, or system, and corresponding method, for manipulating (e.g., compressing or distracting) one or more patient's bones, bone portions, bone fragments, etc.

BACKGROUND

Bone fractures are often repaired by securing an orthopedic implant to one or more patient's bone(s), bone portions, bone fragments, etc. (terms used interchangeably without the intent to limit or distinguish). For example, it is not uncommon for a patient to receive an orthopedic implant such as, for example, a bone plate, to repair one or more fractures in a patient's bone.

During fixation or coupling of the orthopedic implant (e.g., bone plate) to the patient's fractured bone, a surgeon may need to realign, reposition, or move one portion of the fractured bone relative to another portion of the fractured bone. For example, the surgeon may compress the fracture by moving two bone fragments closer together. Alternatively, the surgeon may distract the fracture by moving the bone fragments farther apart.

Generally speaking, reducing/distracting bone fragments during implantation of a bone plate is often done with an orthopedic device, instrument, tool, or system (terms used interchangeably herein without the intent to limit or distract) such as, for example, a bone plate reduction instrument including forceps for applying force to manipulate the position of the patient's bone fragments. In use, one arm of the forceps is arranged and configured to couple to a bone plate. For example, one of the arms of the forceps is arranged and configured to hook into a special opening formed at one end of the bone plate. The other arm of the forceps is coupled to a bone fastener that is inserted into one of the bone fragments through an incision in the patient's skin. In use, to secure the forceps to the bone fragment, the bone fastener is secured to the bone fragment through a hole formed in the arm of the forceps. Thus arranged, tightening or squeezing the arms of the forceps reduces the two bone fragments together.

One disadvantage of conventional forceps is that the instrument is fixedly coupled to the bone fastener inserted into the patient's bone (e.g., the forceps cannot be disengaged from the bone fragment without removing the bone fastener from the patient's bone fragment). In addition, conventional forceps require a dedicated, specialized opening formed in the bone plate to accommodate the arm of the forceps.

It would be advantageous to releasably couple the forceps to the bone fastener used for reduction of the patient's bone fragments (e.g., to enable the forceps to decouple from the bone fastener without requiring the bone fastener to be removed from the patient's bone). In addition, it would be advantageous to eliminate the need for a specialized opening formed in the bone plate. Moreover, it would be beneficial to enable a surgeon to quantify the amount of force being applied to better assist surgeons determine when proper reduction has been achieved. It is with respect to these and other considerations that the present disclosure may be useful.

BRIEF SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

There is provided a tool for manipulating bone segments, including first and second handles pivotably coupled together and first and second engaging arms, the first ends of which are coupled to the first and second handles, respectively, so that when the first and second handles are pivoted relative to one another, the first and second engaging arms move toward and away from one another, a second end of the first and second engaging arms having a threaded bore, the threaded bore of the first engaging arm configured to receive a first bell housing, the threaded bore of the second engaging arm configured to receive a second bell housing, wherein one end of either the first or the second bell housing is configured to engage a fastener hole in a bone plate and the other end of the bell housing is advantageously configured to releasably fit over a head portion of a bone fastener.

In some embodiments, the bone reduction instrument includes a threaded rod coupled to each of the first and second handles. Additionally, the threaded rod may pivot about the first handle and be received in a bore formed in the second handle. In further embodiments, the threaded rod may receive a knurled nut. Tightening the nut over the threaded rod may cause the knurled nut to contact the second handle and urge the first and second handles together. In yet a further embodiment, the knurled nut may contain a biasing element with visual indicators to indicate the force being exerted on the first and second handles. In an additional embodiment, the bone plate reduction instrument may include an electronic force or strain sensor with a local or remote display to indicate the force being placed on bone fragments during reduction. The bone plate reduction instrument may include optical tracking elements for detection by a surgical navigation system. The electronic force or strain sensor may be integrated with a surgical navigation system or robotic surgical system. In yet a further embodiment, the tool may further include a biasing element that urges the first and second handles apart.

In further embodiments, the bell housing may be releasably coupled with the engaging arms with threads, ball detents or any other mechanism.

In one method disclosed, a bone plate may be placed adjacent to two bone fragments and bone fasteners placed in the bone plate to secure one bone fragment to the bone plate. An incision may then be made in the patient's skin near the second bone fragment. A hole is drilled into the second bone fragment through the incision and a bone fastener inserted in the second bone fragment. A fastener hole end of a bell housing may then be coupled to a first engaging arm of a bone plate reduction instrument and a bell end of a second bell housing may be coupled to a second engaging arm of a bone plate reduction instrument. The fastener hole end of the first bell housing couples to a fastener hole at one end of the bone plate and the bell end of the second bell housing hooks over the bone fastener coupled to the second bone fragment. The first and second handles of the bone plate reduction instrument may be urged together to provide a controlled force that reduces the two bone fragments together. Finally, additional fasteners may be placed to secure the bone plate to the second bone fragment.

A bone reduction system for manipulating one or more patient's bone fragments is also disclosed. In one embodiment, the bone reduction system includes a bone reduction instrument and first and second tips. In one embodiment, the bone reduction instrument includes a first handle pivotably coupled to a second handle, the first handle including a first arm, the second handle including a second arm, each of the first and second arms including a coupling mechanism. In one embodiment, the first tip is selectively coupled to the coupling mechanism of the first arm, the second tip is selectively coupled to the coupling mechanism of the second arm. Each of the first and second tips include a first end arranged and configured to mate with a fastener hole formed in a bone plate, a second end arranged and configured to receive a head portion of a bone fastener, and an intermediate portion arranged and configured to couple to the coupling mechanism of the first and second arms.

In one embodiment, the coupling mechanism formed in the first and second arms includes an internally threaded borehole and the intermediate portion of the first and second tips include external threads for threadably engaging the internally threaded borehole formed in the first and second arms.

In one embodiment, the bone reduction system further includes a bone plate including a plurality of fastener holes, the first end of the first and second tips being arranged and configured to engage one of the plurality of fastener holes.

In one embodiment, the bone reduction system further includes a bone fastener, the second end of the first and second tips including an enlarged bell housing including an internal cavity arranged and configured to receive a head portion of the bone fastener.

In one embodiment, the enlarged bell housing includes a circumferential opening in communication with the internal cavity and a ledge, wherein with the head portion of the bone fastener received within the internal cavity, the ledge engages an underside of the head portion of the bone fastener.

In one embodiment, moving the first and second handles toward each other causes the first and second arms to move towards each other.

In one embodiment, the bone reduction instrument further include a locking or tightening mechanism including an externally threaded rod coupled to one of the first and second handles, the externally threaded rod passing through the other one of the first and second handles, and an internally threaded nut arranged and configured to engage the externally threaded nut.

In one embodiment, the bone reduction instrument further includes a force sensor arranged and configured to measure an amount of force being applied to the first and second handles.

In one embodiment, the force sensor includes an outer body including an internally threaded bore arranged and configured to threadably engage the externally threaded rod and a load sensor positioned at an end thereof so that, in use, rotation of the externally threaded nut rotates at least a portion of the force sensor into contact with one of the first and second handles.

In one embodiment, the force sensor further includes one or more springs positioned within the outer body of the force sensor, in use, rotation of the internally threaded nut causes compression of the one or more springs to provide haptic feedback to a user.

In one embodiment, the force sensor further includes indicia on an outer surface thereof to provide visual feedback to a user.

In one embodiment, the indicia includes a plurality of color-coded bands to indicate a level of compression being applied across a bone fracture.

A bone reduction system for manipulating one or more patient's bone fragments is also disclosed. In one embodiment, the bone reduction system includes a bone plate including a plurality of fastener holes, a plurality of bone fasteners including a first fastener for coupling the bone plate to a first bone fragment and a second fastener for coupling to a second bone fragment, a bone reduction instrument, and first and second tips. In one embodiment, the bone reduction instrument includes a first handle pivotably coupled to a second handle, the first handle including a first arm, the second handle including a second arm, each of the first and second arms including a coupling mechanism. In one embodiment, the first tip is selectively coupled to the coupling mechanism of the first arm, the second tip is selectively coupled to the coupling mechanism of the second arm. Each of the first and second tips include a first end arranged and configured to mate with one of the plurality of fastener holes formed in the bone plate, a second end arranged and configured to receive a head portion of the second fastener, and an intermediate portion arranged and configured to couple to the coupling mechanism of the first and second arms.

In one embodiment, the coupling mechanism formed in the first and second arms comprises an internally threaded borehole and the intermediate portion of the first and second tips include external threads for threadably engaging the internally threaded borehole formed in the first and second arms.

In one embodiment, the second end of the first and second tips includes an enlarged bell housing including an internal cavity arranged and configured to receive the head portion of the second fastener.

In one embodiment, the bone reduction instrument further includes a locking or tightening mechanism including an externally threaded rod coupled to one of the first and second handles, the externally threaded rod passing through the other one of the first and second handles, and an internally threaded nut arranged and configured to engage the externally threaded nut.

In one embodiment, the bone reduction instrument further includes a force sensor arranged and configured to measure an amount of force being applied to the first and second handles.

In one embodiment, the force sensor includes an outer body including an internally threaded bore arranged and configured to threadably engage the externally threaded rod and a load sensor positioned at an end thereof so that, in use, rotation of the externally threaded nut rotates at least a portion of the force sensor into contact with one of the first and second handles.

In one embodiment, the force sensor further includes one or more springs positioned within the outer body of the force sensor, in use, rotation of the internally threaded nut causes compression of the one or more springs to provide haptic feedback to a user.

In one embodiment, the force sensor further includes indicia on an outer surface thereof to provide visual feedback to a user.

In one embodiment, the indicia includes a plurality of color-coded bands to indicate a level of compression being applied across a bone fracture.

A method for reducing a bone fracture is also disclosed. In one embodiment, the method includes coupling a bone plate to a first bone fragment of a patient's bone, implanting a bone fastener into a second bone fragment of the patient's bone, coupling a bone reduction instrument to the bone plate and the bone fastener, wherein the bone reduction instrument includes interchangeable first and second tips, each of the first and second tips including a first end to couple with a fastener hole formed in the bone plate, a second end to receive a head portion of the bone fastener, and an intermediate portion arranged and configured to couple to the bone reduction instrument, and compressing first and second handles of the bone reduction instrument to compress the bone fracture positioned between the first and second bone fragments, wherein the bone reduction instrument is arranged and configured to decouple from the bone fastener and the bone plate without requiring the bone fastener to be removed from the second bone fragment.

In one embodiment, the bone reduction instrument includes a first handle pivotably coupled to a second handle, the first handle including a first arm, the second handle including a second arm, each of the first and second arms including a coupling mechanism arranged and configured to engage one of the first and second tips.

In one embodiment, the coupling mechanism formed in the first and second arms comprises an internally threaded borehole and the intermediate portion of the first and second tips include external threads for threadably engaging the internally threaded borehole formed in the first and second arms.

In one embodiment, the method further includes measuring a force applied across the bone fracture and determining whether the force falls within a predetermined acceptable range.

Embodiments of the present disclosure provide numerous advantages. For example, conventional bone plate reduction instruments require the bone fastener to be inserted through a hole or an opening formed in one of the arms of the bone plate reduction instrument, effectively trapping or fixedly coupling the bone plate reduction instrument to the bone fastener, which is coupled to the patient's bone fragment. As such, the bone plate reduction instrument cannot be decoupled from the bone fastener without removing the bone fastener from the patient's bone fragment. In accordance with one or more features of the present disclosure, the bone plate reduction instrument allows the bone plate reduction instrument to be releasably coupled to the bone fastener, thereby enabling a surgeon to quickly release or disconnect the bone plate reduction instrument from the bone plate and bone fastener once reduction has been completed. Thus arranged, a surgeon could perform further reduction, if needed, without having to reinsert a bone fastener. Additionally, conventional bone plates include a specialized, dedicated opening for coupling to the bone plate reduction instrument, which requires additional manufacturing steps and use of valuable real estate on the bone plate. In accordance with one or more features of the present disclosure, the bone plate reduction instrument is arranged and configured to utilize a standard fastener hole formed in the bone plate. In addition, the selectively, repositionable tips (e.g., bell housing) of the present disclosure are universal, reducing the need for an operating room technician to search for discrete instruments.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figures 1, 2:
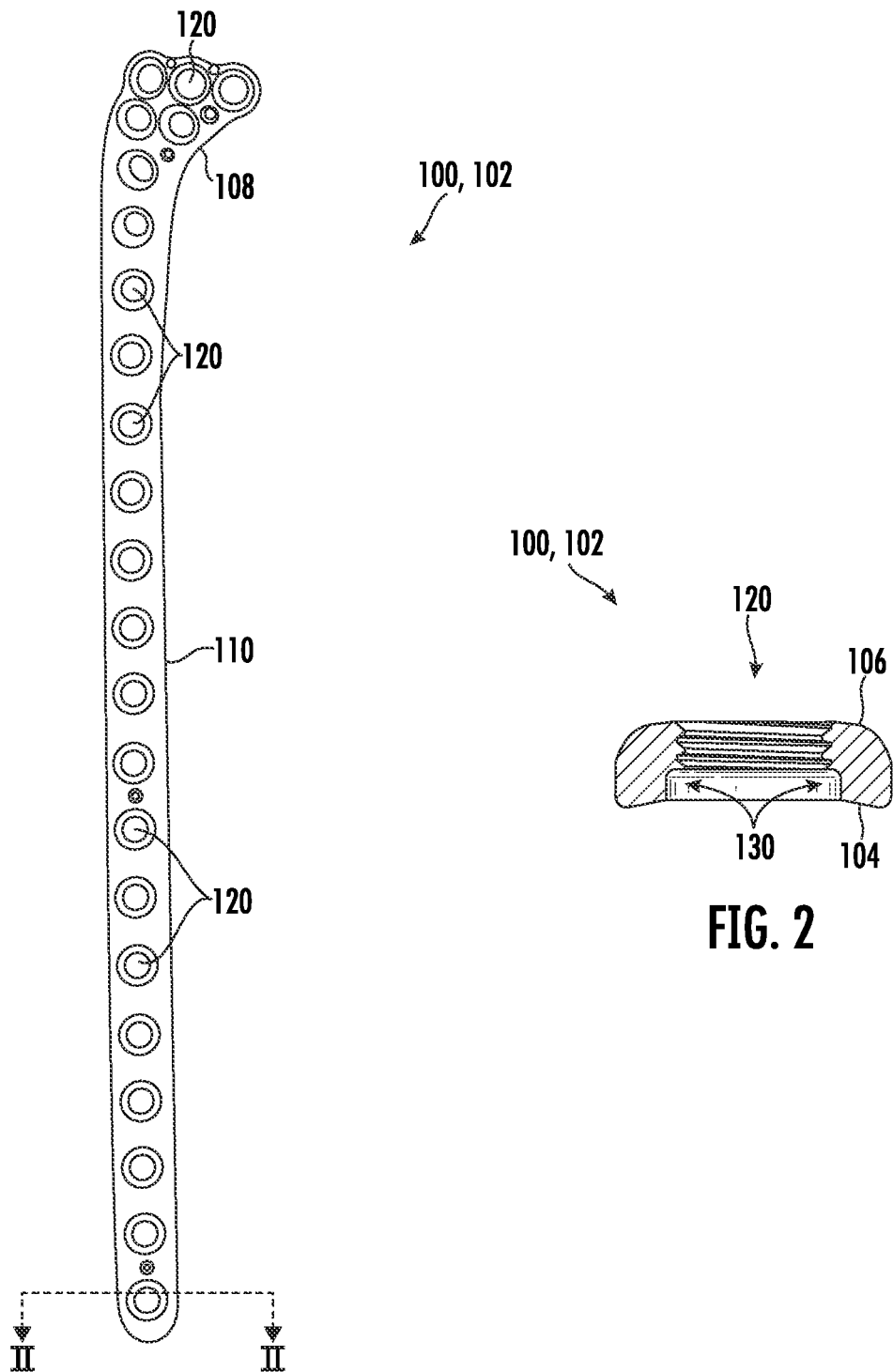
FIG. 1 illustrates a top view of a bone plate that may be used in combination with a bone plate reduction instrument in accordance with one or more features of the present disclosure.
FIG. 2 illustrates a cross sectional view of the bone plate shown in FIG. 1 taken along line II-II in FIG. 1.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

Various features of an orthopedic device, instrument, tool, or system (terms used interchangeably herein without the intent to limit or distinguish) for manipulating (e.g., compressing or distracting) one or more patient's bones, bone portions, bone fragments, etc. (terms used interchangeably herein without the intent to limit or distinguish), will now be described more fully hereinafter with reference to the accompanying drawings, in which one or more features of the orthopedic instrument (referred to herein as a bone plate reduction instrument or bone reduction instrument) will be shown and described. It should be appreciated that the various features may be used independently of, or in combination, with each other. It will be appreciated that the bone plate reduction instrument as disclosed herein may be embodied in many different forms and should not be construed as being limited to the embodiments set forth herein. Rather, these embodiments are provided so that this disclosure will convey certain features of the bone plate reduction instrument to those skilled in the art.

It should be understood that, as described herein, an "embodiment" (such as illustrated in the accompanying Figures) may refer to an illustrative representation of an environment or article or component in which a disclosed feature may be provided or embodied, or to the representation of a manner in which just the feature may be provided or embodied. However, such illustrated embodiments are to be understood as examples (unless otherwise stated), and other manners of embodying the described features, such as may be understood by one of ordinary skill in the art upon learning the features from the present disclosure, are within the scope of the disclosure. In addition, it will be appreciated that while the Figures may show one or more embodiments of features together in a single embodiment of an environment, article, or component incorporating such features, such features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

Disclosed herein are various bone plate reduction instruments including one or more features arranged and configured to facilitate compression or distraction across a patient's bone fracture. As will be described and illustrated herein, the bone plate reduction instrument may be used to compress a patient's bone fracture. However, it will be understood by one of ordinary skill in the art, that the bone plate reduction instrument could also be used to distract the patient's bone fracture if needed. In addition, in one embodiment, the bone plate reduction instrument may be used without a bone plate. For example, the bone plate reduction instrument may be used in combination with a pair of bone fasteners. As such, the bone plate reduction instrument should not be limited to reduction/compression and/or used in combination with a bone plate unless explicitly claimed.

In one embodiment, as will be described in greater detail herein, the bone plate reduction instrument includes forceps having first and second arms associated with first and second handles, respectively. Each arm including a coupling mechanism such as, for example, a threaded end piece or borehole. In addition, the bone plate reduction instrument includes first and second devices, components, or tips referred to herein as bell housings. Thus arranged, in use, the forceps is arranged and configured with interchangeable tips or bell housings with each tip or bell housing including a first end arranged and configured to mate with a fastener hole or opening formed in a bone plate, a second end arranged and configured to receive a head portion of a bone fastener, and an intermediate portion arranged and configured to couple to the coupling mechanism such as, for example, including an intermediate threaded portion arranged and configured to threadably engage the threaded borehole formed in the first and second arms of the forceps. In addition, in accordance with one or more features of the present disclosure, the bone plate reduction instrument may include a force sensing mechanism or gauge arranged and configured to measure an amount of force being applied to assist with determining when proper reduction across a bone fracture has been achieved. In use, the force may be provided as a local readout. Alternatively, the force can be transmitted as a signal, which can be uploaded to a surgical navigation system, a camera, a computer, a laptop, a mobile device, etc.

Referring to FIGS. 1 and 2, in accordance with one or more features of the present disclosure, as will be described in greater detail herein, in use, the bone plate reduction instrument may be used in combination with an orthopedic implant or bone fixation device 100, which may be any suitable device now known or hereafter developed for fixing or coupling to a fractured bone. As illustrated, in one embodiment, the orthopedic implant or bone fixation device 100 may be a bone plate 102. In use, the bone plate 102 is arranged and configured for positioning adjacent to a patient's bone such as, for example, a fractured bone. In use, the bone plate 102 may be provided in any suitable shape and/or configuration, which, as will be appreciated by one of ordinary skill in the art, may be dependent on the location and type of patient's bone being fixed. For example, the bone plate 102 may be arranged and configured to span, contact, etc. a distal femur, a proximal femur, a distal tibia, a proximal tibia, a proximal humerus, a distal humerus, a fibula, an ulna, a radius, a distal radius, bones of the foot, or bones of the hand, shaft fractures on long bones, etc.

In one embodiment, as illustrated, the bone plate 102 may include a lower or bone facing surface 104 and an upper surface 106. In addition, the bone plate 102 may include a head portion 108 and a shaft portion 110. Moreover, the bone plate 102 includes a plurality of fastener holes or openings 120 (terms used interchangeably herein without the intent to limit or distinguish) formed therein for receiving a plurality of bone fasteners or screws (terms used interchangeably herein without the intent to limit or distinguish) for coupling the bone plate 102 to the patient's bone. In various embodiments, one or more of the fastener holes 120 may include an undercut or counterbore 130 (e.g., an enlarged diameter portion forming a ledge or shelf).

In one embodiment, the fastener holes 120 may be in the form of a locking fastener (or screw) hole. That is, as will be appreciated by one of ordinary skill in the art, locking fastener holes include a plurality of threads formed on an inner surface thereof for mating with threads formed on an outer surface of a head portion of a bone fastener. Thus arranged, the bone fastener may be said to be locked to the bone plate 102 via the locking fastener holes. That is, as will be appreciated by one of ordinary skill in the art, the bone fastener is threaded through one of the locking fastener holes formed in the bone plate 102 and into the patient's bone. The bone fastener is secured to the bone plate 102 via threads formed on the head portion of the bone fastener that cooperate with the threaded locking fastener hole formed in the bone plate 102. This secures the bone plate 102 with respect to the patient's bone and provides rigid fixation between the bone plate 102 and the bone fasteners. However, it should be appreciated that the fastener holes 120 may have other configurations such as, for example, variable angled fastener holes, which are non-threaded and enable the bone fastener to be angled relative to the bone plate. As will be appreciated by one of ordinary skill in the art, the number of fastener holes 120 can be variable depending on the length of the plate.

In addition, and/or alternatively, the bone plate 102 may be manufactured from any suitable material now known or hereafter developed, including, for example, metals, polymers, plastics, ceramics, resorbable, non-resorbable, composite materials, etc. Suitable materials may include, for example, titanium, stainless steel, cobalt chrome, polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a patient's body. In some embodiments, the bone fastener may be manufactured from the same material as the bone plate. In other embodiments, the fasteners may be manufactured from a different material as compared to the bone plate.

The fastener can be any type of fastener now known or hereafter developed. For example, the fastener may include any type of external thread including standard or non-standard threads. For example, the external threads can be arranged as a continuous ridge or a non-continuous ridge. The external threads can form a portion of a revolution, one complete revolution, multiple revolutions, a single lead, multiple leads, or any other threads known in the art. Additionally, and/or alternatively, in the case of locking fasteners, the head portion of the bone fastener can include any surface that will engage with and seat within a locking fastener hole formed in the bone plates. For example, the head portion can include threads. Alternatively, the head portion can include a series of dimples, ridges, bumps, textured areas, or any other surface that can secure the fastener.

The fastener may be any fastener now known or hereafter developed, made out of any appropriate material now known or hereafter developed. The fastener may include a bore for receiving a driver in order to drive the fastener through the bone fixation plate and into the patient's bone. The bore may be any size and shape, for example, it may have a hexagonal configuration to receive a corresponding hexagonal driver, a Phillips screw head, a flat-head, a star configuration, Torx, or any other appropriate configuration that can cooperate with a driver to drive the fastener through the bone plate and into the patient's bone.

The shaft of the fastener may be fully threaded, partially threaded, or a helical blade, and/or may include one or more tacks, deployable talons, expandable elements, or any feature that allows the shaft to engage the patient's bone. It is also possible that shaft be non-threaded so that the fastener takes the form of a peg or a pin. The end of the shaft may be a self-tapping or self-drilling tip.

Figure 3:
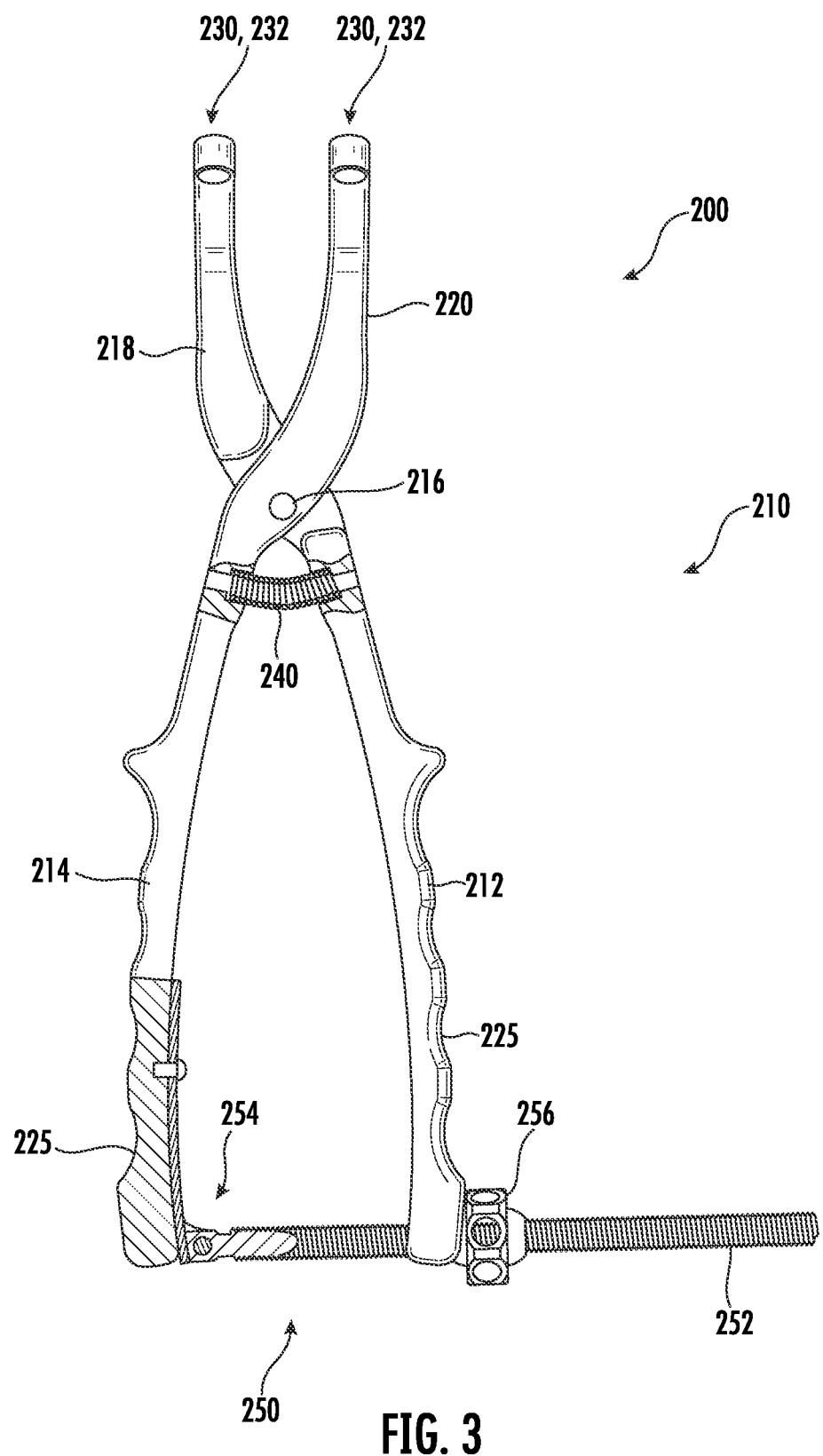
FIG. 3 illustrates a top view of an embodiment of a bone plate reduction instrument in accordance with one or more features of the present disclosure.
Figure 4A:
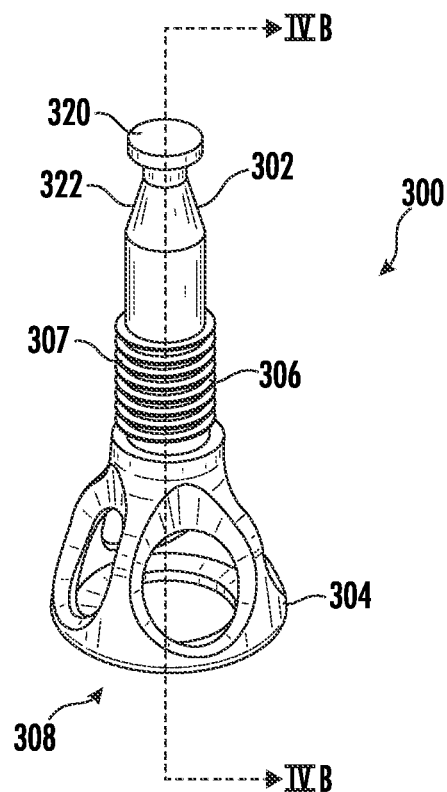
FIG. 4A illustrates a perspective view of an embodiment of a reversible tip or bell housing in accordance with one or more features of the present disclosure.
Figure 4B:
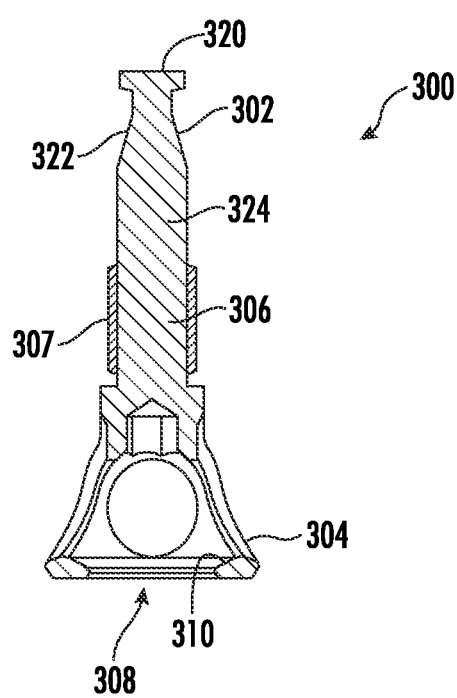
FIG. 4B illustrates a cross-sectional view of the reversible tip or bell housing plate shown in FIG. 4A taken along line IVB-IVB in FIG. 4A.
Figure 5:
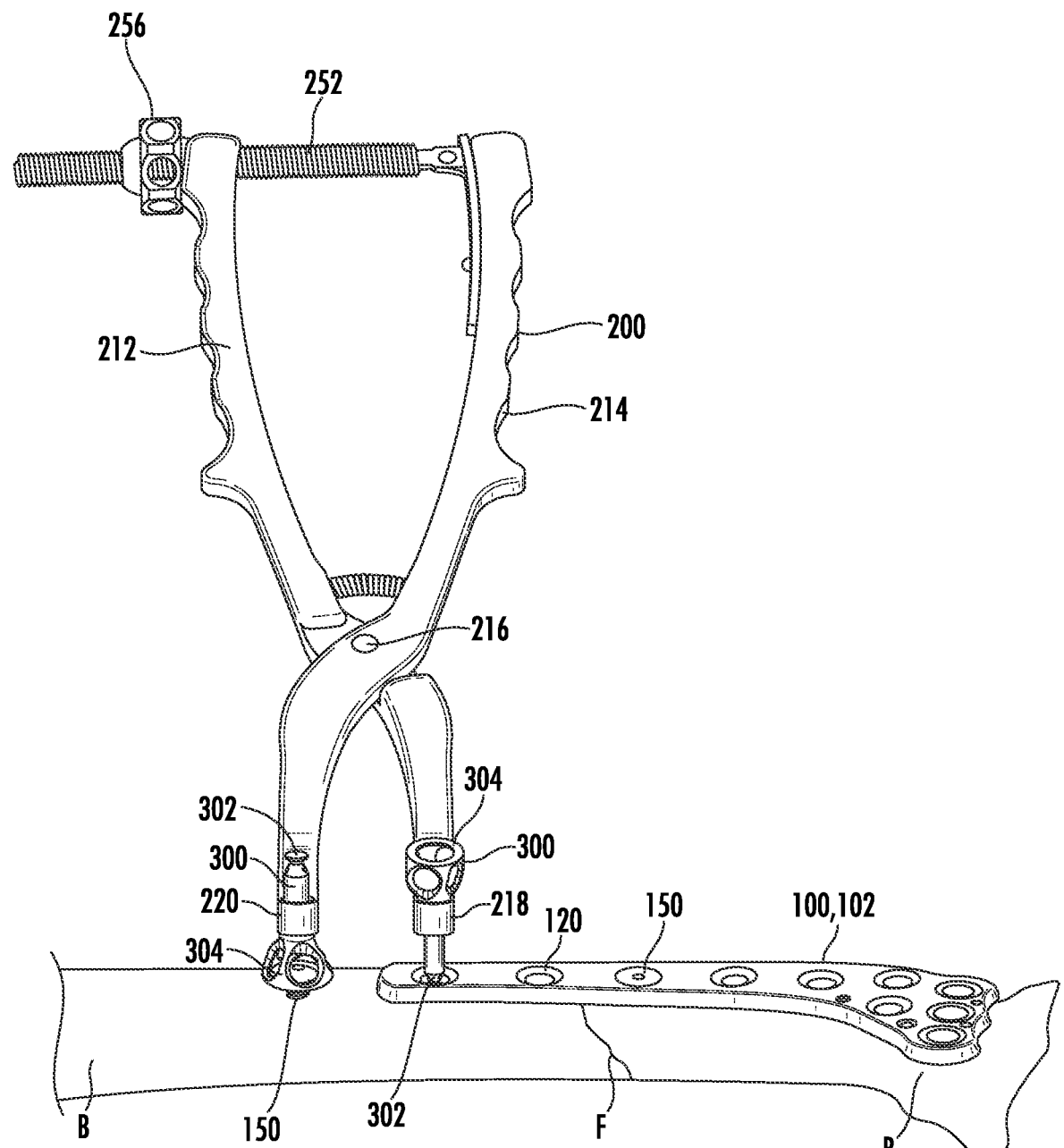
FIG. 5 illustrates a perspective view of the bone plate reduction instrument shown in FIG. 3 coupled to a bone plate.

Referring to FIGS. 3-5, in accordance with one or more features of the present disclosure, an example of an embodiment of a bone plate reduction instrument 200 is illustrated. As illustrated, in one embodiment, the bone plate reduction instrument 200 may be provided in the form of a plier-like device or tool or forceps 210 (terms used interchangeably herein without the intent to limit or distinguish) including a first handle 212 and a second handle 214 pivotably coupled to each other via an intermediate pivot point or hinge 216. Thus arranged, the forceps 210 further include first and second arms 218, 220, respectively. That is, as will be readily appreciated by one of ordinary skill in the art, the distal portion of the first and second handles 212, 214 positioned distally of the pivot pin 216 define first and second arms 218, 220. As illustrated, in one embodiment, the first handle 212 may be integral or monolithic with the first arm 218. The second handle 214 may be integral or monolithic with the second arm 220. Alternatively, the arms 218, 220 may be separate from the handles 212, 214 and coupled together. In one embodiment, the first and second arms 218, 220 may be parallel with the first and second handles 218, 220. Alternatively, the first and second arms 218, 220 may be perpendicular, or arranged at some angle relative to the first and second handles 218, 220.

In use, movement of the first and second handles 212, 214 causes movement of the first and second arms 218, 220. For example, in one embodiment, moving (e.g., squeezing or compressing) the first and second handles 212, 214 together causes the first and second arms 218, 220 to compress together. In one embodiment, as illustrated, the first and second handles 212, 214 may include an ergonomic surface 225 to facilitate improved gripping by the user.

In accordance with one or more features of the present disclosure, the first and second arms 218, 220 each include a coupling mechanism 230 formed at an end thereof, the coupling mechanism 230 being arranged and configured to engage a bell housing 300 as will be described in greater detail below. In one embodiment, the coupling mechanism 230 may be provided in the form of a bore 232 having internal threads for engaging external threads formed on the bell housing 300. However, other suitable coupling mechanisms 230 may be used including, for example, a taper connection, spring ball detents, a collet with external threads, etc.

In one embodiment, the forceps 210 may also include a spring 240 such as, for example, a compression spring, positioned between the first and second handles 212, 214. In one embodiment, the spring 240 may be positioned adjacent to the pivot pin 216. In use, the spring 240 is arranged and configured to provide resistance to compressing the first and second handles 212, 214.

In one embodiment, the forceps 210 may also include a locking or tightening mechanism 250. In use, the locking or tightening mechanism 250 may be provided in any suitable form, configuration, or mechanism now known or hereafter developed. For example, a ratchet mechanism, a rack and pawl mechanism, or the like. As illustrated, in one embodiment, the locking or tightening mechanism 250 may include an externally threaded rod 252. In use, a first end of the threaded rod 252 may be coupled to one of the first and second handles 212, 214 (e.g., shown as being coupled to the second handle 214). In addition, the threaded rod 252 is arranged and configured to pass through the other of the first and second handles 212, 214 (e.g., shown as passing through the first handle 212). The threaded rod 252 may be coupled by any suitable mechanism now known or hereafter developed. For example, as illustrated, the end of the threaded rod 252 may be coupled to the second handle 214 via a pivot pin 254 so that, in use, the threaded rod 252 can pivot about pivot pin 254. In addition, the handle (e.g., first handle 212) may be configured to enable the threaded rod 252 to pass therethrough via any suitable mechanism now known or hereafter developed. For example, the first handle 212 may include a bore or slot formed in the end thereof so that the threaded rod 252 can pass therethrough. The locking or tightening mechanism 250 may also include a nut 256 such as, an internally threaded knurled nut, for threadably engaging the externally threaded rod 252. Thus arranged, in use, with the nut 256 abutting an outer surface of the first handle 212 rotation of the nut 256 tightens, compresses, moves, etc. the first handle 212 towards the second handle 214. That is, rotation of the nut 256 applies a force to move the first and second handles 212, 214 together, which in turn forces first and second arms 218, 220 together.

In addition, as will be appreciated by one of ordinary skill in the art, the locking or tightening mechanism 250 also facilitates maintaining a desired compression position of the forceps 210. That is, in use, movement of the nut 256 along the threaded rod 252 selectively inhibits movement of the first handle 212 away from the second handle 214 and thus maintains the bone portions in the desired position. In addition, a second nut 256 (FIG. 8) positioned along the threaded rod 252 in-between the first and second handles 212, 214 could be utilized to distract the first and second handles 212, 214 and/or to inhibit movement of the first handle 212 towards the second handle 214.

The forceps 210 may be manufactured by any suitable material such as, for example, a metal such as stainless steel, titanium, medical grade polymers, etc. While a particular embodiment of a bone plate reduction instrument or forceps has been shown and described, it will be appreciated that the bone plate reduction instrument or forceps may have alternate configurations.

Referring to FIGS. 4A and 4B, in accordance with one or more features of the present disclosure, an example embodiment of a tip or a bell housing 300 is illustrated. In use, as will be described in greater detail, the bell housing 300 is arranged and configured to selectively and releasably engage either a bone fastener or a bone plate. In addition, the bell housing 300 is arranged and configured to engage the coupling mechanism 230 formed on the first and second arms 218, 220 of the forceps 210. Thus arranged, the surgeon has increased flexibility to selectively and releasably engage either a bone fastener or a bone plate as needed. In addition, the surgeon can decouple or disconnect the forceps 210 from the bone fastener and the bone plate without having to remove the bone fastener from the patient's bone.

With continued reference to FIGS. 4A and 4B, the bell housing 300 includes a first end 302, a second end 304, and an intermediate portion 306. In use, the first end 302 is arranged and configured to engage a bone plate such as, for example, bone plate 102. In one embodiment, the first end 302 is arranged and configured to be received with one of the fastener holes 120 formed in the bone plate 102. For example, in one embodiment, the first end 302 of the bell housing 300 may be arranged and configured to fit into the undercut or counterbore 130 formed in the fastener hole 120 of the bone plate 102. Thus arranged, the bell housing 300 can be selectively coupled to a bone plate 102 without requiring the bone plate 102 to include a specialized opening for receiving the bone plate reduction instrument 200.

As illustrated, on one embodiment, the first end 302 includes an enlarged circumferential end portion or tip 320. In addition, the first end 302 may include a tapered portion 322 extending from the intermediate portion 306 to the enlarged circumferential end portion or tip 320. The tapered portion 322 tapering from a larger diameter adjacent to the intermediate portion 306 to a smaller diameter adjacent to the enlarged circumferential end portion or tip 320. The enlarged circumferential end portion or tip 320 may have a diameter equal to or substantially similar to the diameter of the intermediate portion 306. Thus arranged, the first end 302 is arranged and configured to engage a standard fastener hole 120 formed in the bone plate 102, and more specifically, the enlarged circumferential end portion or tip 320 is arranged and configured to be received within the undercut or counterbore 130 formed in the fastener hole 120 of the bone plate 102. In use, when subjected to compression and/or tension, the enlarged circumferential end portion or tip 320 prevents the first end 302 of the bell housing 300 from disengaging from the bone plate 102.

In one embodiment, the intermediate portion 306 may include external threads 307 arranged and configured to engage the internally threaded bores 232 formed in the first and second arms 218, 220 of the forceps 210, although as previously mentioned other suitable coupling mechanisms may be used. In one embodiment, as generally illustrated, the bell housing 300 may be provided in the form of a shaft 324 extending from the first end 302 towards the second end 304. The shaft 324 may be integrally formed and may include the first end 302 inclusive of the enlarged circumferential end portion or tip 320 and the tapered portion 322 and the external threads 307 of the intermediate portion 306. In one embodiment, the second end 304 may be integrally formed with the shaft 324, or may be separately formed and coupled thereto.

In one embodiment, the second end 304 of the bell housing 300 is arranged and configured to receive a head portion of a bone fastener. For example, as illustrated, the second end 304 of the bell housing 300 may include an internal cavity 308 arranged and configured to receive or snap-fit over a head portion of a bone fastener. In one embodiment, the bell housing 300 may include a ledge 310 extending along a circumferential opening at the second end 304, the ledge 310 arranged and configured to releasably capture a head portion of the bone fastener. In addition, in one embodiment, the second end 304 may be rendered expandable and/or flexible so that the head portion of the bone fastener can be readily inserted into the internal cavity 308 of the bell housing 300 where it can be captured by the ledge 310. Thus arranged, advantageously, either end 302, 304 of the bell housing 300 may be used in surgery to connect to either a bone plate or a bone fastener as desired.

With reference to FIG. 5, an example method of use will now be shown and described. In one embodiment, as illustrated, the patient's bone B may be broken thus defining a fracture F on either side of a bone segment. During surgery, it may be necessary for the surgeon to reduce or compress the fracture F by moving the bone segments closer together. In one embodiment, a bone plate such as, for example, bone plate 102, may be positioned onto the patient's bone B across the fracture F. In one embodiment, a bone fastener 150 may be inserted through one of the fastener holes 120 formed in the bone plate 102 and into one of the bone fragments.

Next, a second bone fastener 150 may be inserted into the other bone fragment. For example, in one embodiment, a stab incision may be made through the patient's skin in the area of the bone fragment and the bone fastener 150 may be inserted therein.

In one embodiment, with the bone plate 102 coupled to one bone fragment and a second bone fastener 150 coupled to the other bone fragment, a first bell housing can be coupled to the bone plate 102 while a second bell housing 300 can be coupled to the second bone fastener 150, which is directly received within the patient's bone fragment. For example, as illustrated and as previously described, first and second bell housings 300 can be coupled to the first and second arms 218, 220 of the forceps 210. The first bell housing 300 being arranged so that the first end 302 of the bell housing 300 extends distally from the forceps 210 while the second bell housing 300 is arranged so that the second end 304 extends distally from the forceps 210. Thereafter, the first end 302 of the first bell housing 300 can be inserted into one of the fastener holes 120 formed in the bone plate 102. The second end 304 of the second bell housing 300 can be fitted over the head portion of the second bone fastener 150 so that the head portion of the bone fastener 150 is received within the internal cavity 308. At this stage, the forceps 210 is secured to the bone plate 102 and the bone fragment, and the surgeon may squeeze (e.g., compress) the first and second handles 212, 214 together. Alternatively, or in addition, the surgeon may turn the nut 256 to apply a controlled force to reduce and maintain the patient's bone fragments. Once reduction is accomplished, the surgeon may place additional bone fasteners through the bone plate 102 as needed. In addition, the bone plate reduction instrument 200 or forceps 210 may be easily removed from the bone plate 102 and the bone fastener 150 without requiring the second bone fastener 150 to be removed from the patient's bone fragment.

In accordance with one or more features of the present disclosure, the bone plate reduction instrument 200 or forceps 210 may include, or be operatively associated with, a force sensing mechanism, a force sensor, or gauge (terms used interchangeably herein without the intent to limit or distinguish) arranged and configured to sense, measure, determine, or the like, the amount of force being applied to, for example, compress the fracture. That is, by incorporating a force sensor, the bone plate reduction instrument 200 or forceps 210 can measure and/or provide an actual reading to the surgeon of the amount of compression force being applied across the fracture F. In use, the amount of force or reading can be indicated on the force sensor or can be transmitted to, for example, a surgical navigation system, a camera, a computer, a laptop, a mobile device, etc. Thus arranged, using the amount of force or readings, the surgeons can determine if the force being applied across the fracture F falls within predetermined, acceptable known ranges.

Figure 6:
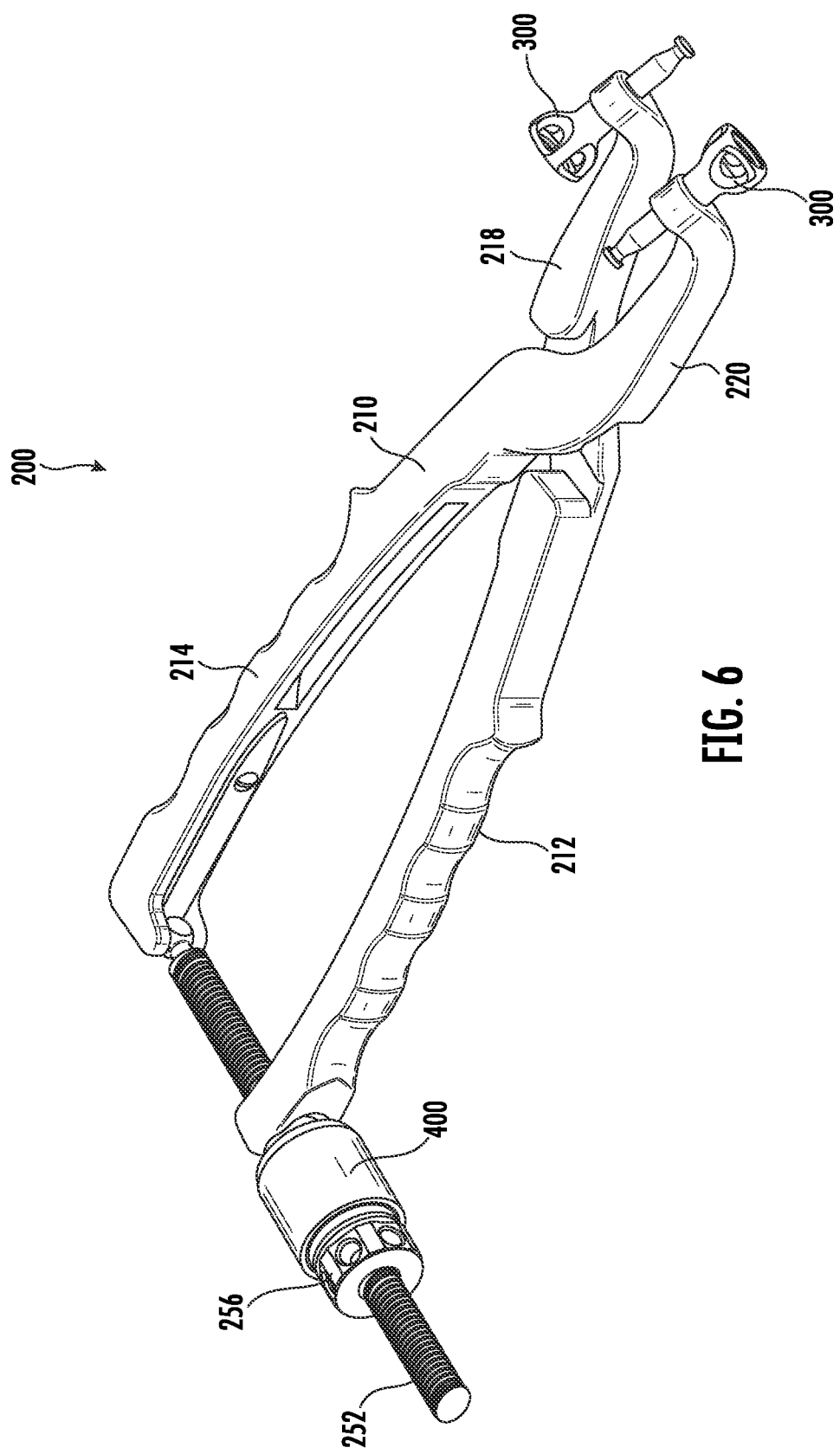
FIG. 6 illustrates a perspective view of an alternate embodiment of a bone plate reduction instrument in accordance with one or more features of the present disclosure, the bone plate reduction instrument including a force sensor.
Figure 7A:
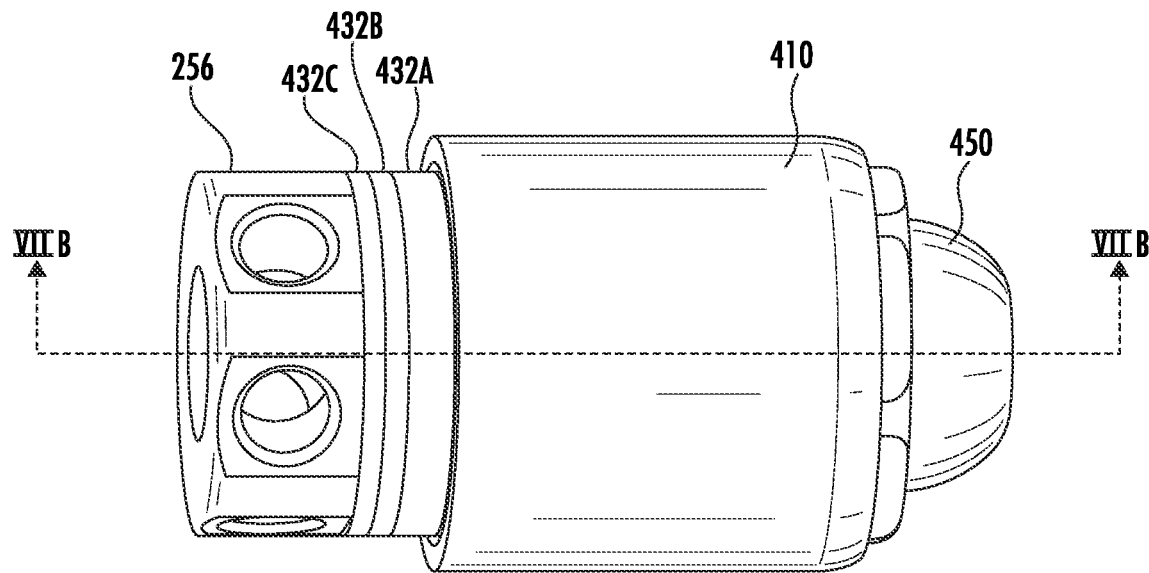
FIG. 7A illustrates a perspective view of an embodiment of the force sensor used in connection with the bone plate reduction instrument shown in FIG. 6.
Figure 7B:
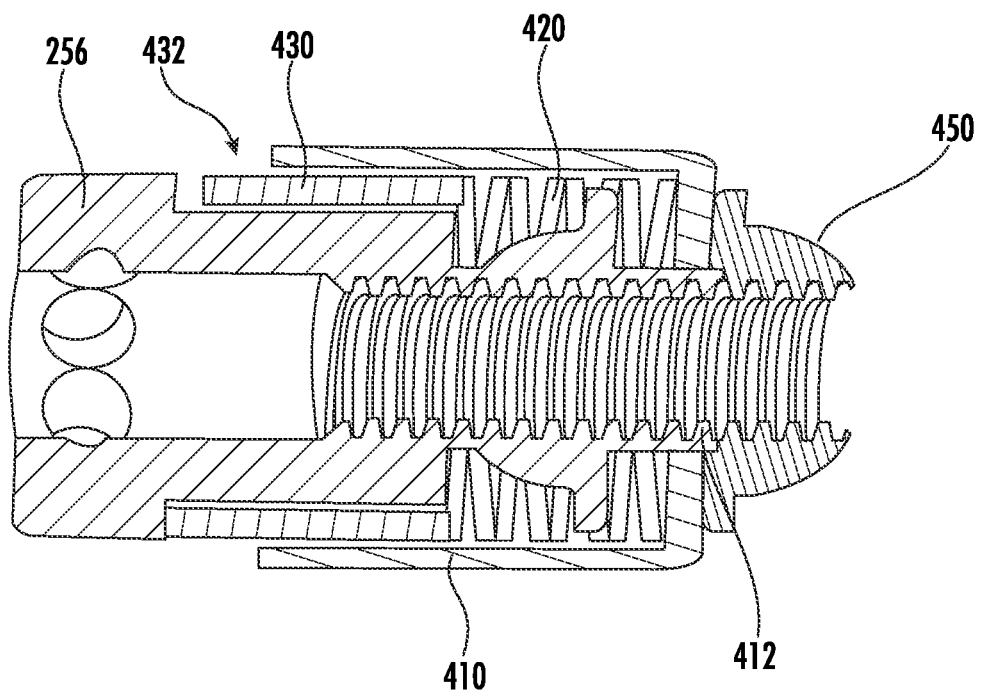
FIG. 7B illustrates a cross-sectional view of the force sensor shown in FIG. 7A taken along line VIIB-VIIB in FIG. 7A.
Figure 8:
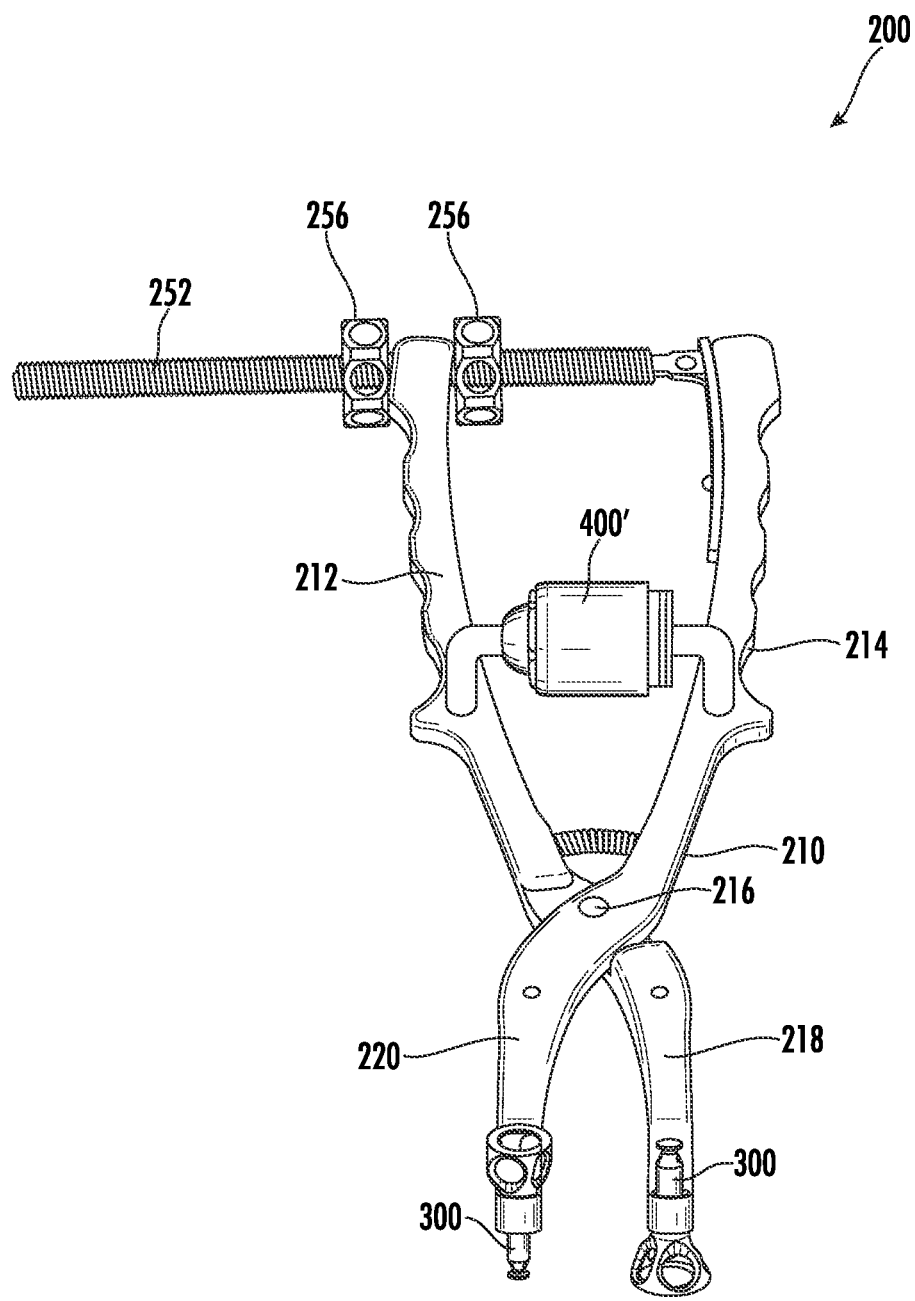
FIG. 8 illustrates a side view of an alternate embodiment of a bone plate reduction instrument in accordance with one or more features of the present disclosure, the bone plate reduction instrument including an alternate embodiment of a force sensor.

In use, the force sensor may have any suitable form now known or hereafter developed. With reference to FIGS. 6-8, an example embodiment of a force sensor 400 in accordance with one or more features of the present disclosure is illustrated. As shown, in one embodiment, the force sensor 400 is arranged and configured to be received on the externally threaded rod 252. In use, the force sensor 400 may be positioned on the threaded rod 252 against the outer surface of the handle (e.g., shown as first handle 212) of the forceps 210. As illustrated, in one embodiment, the force sensor 400 may be combined with the nut such as, for example, nut 256, for engaging the threaded rod 252 (e./g., the nut 256 is built-into the force sensor 400). In use, the force sensor or integrated nut may include hex faces such that the user might turn the entire sensor. Alternatively, it is envisioned that the nut may be separately formed and that the force sensor 400 may be positioned in-between the outer surface of the handle of the forceps 210 and the nut 256.

As illustrated, in one embodiment, the force sensor 400 may include an outer body 410 including an internally threaded bore 412 arranged and configured to threadably engaging the threaded rod 252. In addition, the force sensor 400 includes a load sensor 450. As illustrated, in one embodiment, the load sensor 450 may be positioned at one end thereof to contact, for example, the first handle 212 of the forceps 210. In use, the load sensor 450 is arranged and configured to measure the amount of force being applied. In use, the force sensor 400 and/or the load sensor 450 may be arranged and configured to connect to a local or wireless electronic readout to measure the force. In addition, optical trackers may be placed on the bone plate reduction instrument 200 or forceps 210 to enable to the instrument to be used in a navigated or robotic surgery.

In addition, and/or alternatively, the force sensor 400 may include one or more springs 420 such as, for example, Bellville springs, although other configurations of springs are envisioned. The force sensor 400 may further include an inner body or base portion 430 that may be operatively associated with the nut 256, which as previously mentioned may be integrated into the force sensor 400 (as generally illustrated in FIGS. 6, 7A, and 7B) or may be separately provided. In use, rotation of the nut 256 causes compression of the springs 420 positioned within the outer body 410 of the force sensor 400. This compression provides haptic feedback to the user.

In addition, and/or alternatively, the inner body or base portion 430 may include various indicia 432 located on an outer surface thereof to provide visual feedback to the user. In use, rotation of the nut 256 causes relative movement of the inner body or base portion 432 relative to the outer body 410 in proportion to the amount of force being applied. The indicia 432 may have any suitable form now known or hereafter developed. For example, in one embodiment, the indicia 432 may include color-coded bands of indicia 432A, 432B, 432C such as, for example, green, yellow, and red to provide visual feedback as to the adequacy of the compression force being applied. In use, as the user rotates the nut 256, the indicia 432A, 432B, 432C becomes covered or uncovered, depending on the level of force being applied. For example, in one embodiment, visualization of the red band 432C may indicate that not enough force has been applied to compress the fracture, visualization of the green band 432B may indicate that enough force has been applied to compress the fracture, and yellow band 432A may indicate an intermediate range or that too much compression has been provided. In use, the indicia 432 may be used by the surgeon to indicate the amount of reduction force they are applying to the bone fragments being reduced.

In addition, in one embodiment, the force sensor 400 may be positioned on either side of the handles. That is, while FIG. 6, illustrates a single force sensor 400 positioned against the outer surface of the first handle 212, the force sensor 400 may be positioned along the threaded rod 252 in-between the first and second handles 212, 214. Thus arranged, the amount of force being applied to distract the bone fragments may be measured. Alternatively, the forceps 210 may include dual force sensors 400, one positioned on either side of the first handle 212.

In addition, as schematically illustrated in FIG. 8, in one embodiment, the force sensor 400' may be arranged and configured to be positioned at a different location on the bone plate reduction instrument 200. For example, as illustrated, in one embodiment, the force sensor 400' may be directly coupled to the first and second handles 212, 214.

Figure 9:
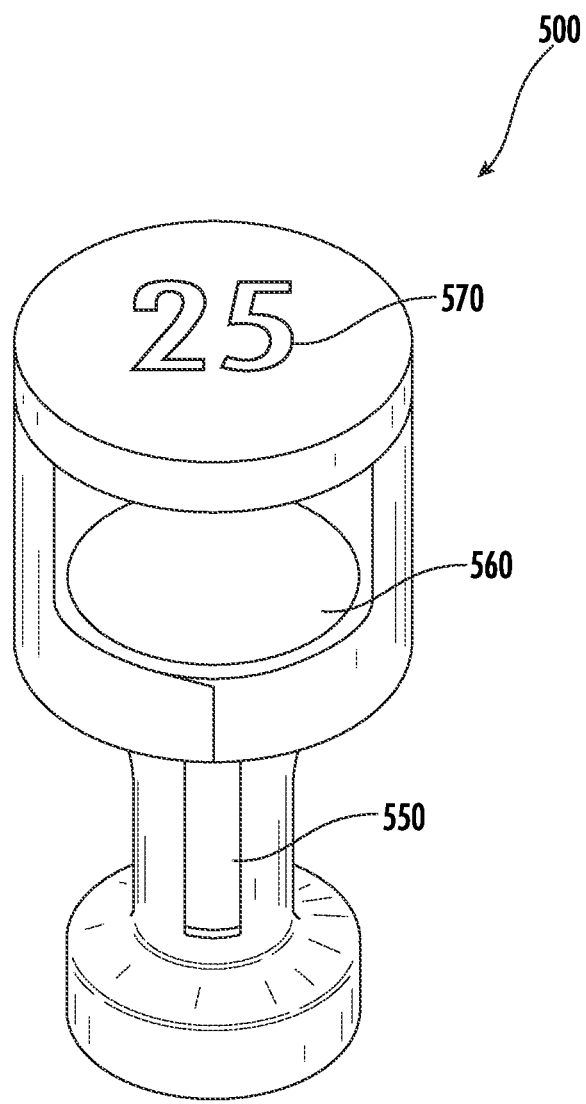
FIG. 9 illustrates a side view of an alternate embodiment of a force sensor in accordance with one or more features of the present disclosure.

Alternatively, with reference to FIG. 9, in accordance with one or more features of the present disclosure, yet another alternate embodiment of a force sensor 500 is illustrated. As illustrated, the force sensor 500 may be provided in the form of a strain gauge incorporated into the tips or bell housings such as, for example, bell housing 300 as previously described. In use, the strain gauge includes a load sensor 550, a battery 560, and a digital readout 570. In use, the force sensor 500 may be used to measure the force applied to the bone fragments, the measured force being displayed on the digital readout 570. In addition, optical trackers may be placed on the bone plate reduction instrument 200 to enable to the instrument to be used in a navigated or robotic surgery. Alternatively, and/or in addition, it is envisioned that a strain gauge may be positioned within the first and second arms 218, 220 of the forceps 210.

The foregoing description has broad application. Accordingly, the discussion of any embodiment is meant only to be explanatory and is not intended to suggest that the scope of the disclosure, including the claims, is limited to these example embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

Terms such as "substantially" and "approximately" are intended to cover minor deviations such as plus or minus 10 percent dimensional variant.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation.

All directional references (e.g., proximal, distal, upper, underside, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

What is claimed is:

1. A bone reduction system for manipulating one or more patient's bone fragments, the bone reduction system comprising:
    a bone reduction instrument including a first handle pivotably coupled to a second handle, the first handle including a first arm, the second handle including a second arm, each of the first and second arms including a coupling mechanism; and
    a first tip selectively coupled to the coupling mechanism of the first arm, and a second tip selectively coupled to the coupling mechanism of the second arm, wherein each of the first and second tips include:
        a first end arranged and configured to mate with a fastener hole formed in a bone plate;
        a second end arranged and configured to receive a head portion of a bone fastener; and
        an intermediate portion arranged and configured to couple to the coupling mechanism of the first and second arms.

2. The bone reduction system of claim 1, wherein the coupling mechanism formed in the first and second arms comprises an internally threaded borehole and the intermediate portion of the first and second tips include external threads for threadably engaging the internally threaded borehole formed in the first and second arms.

3. The bone reduction system of claim 1, further comprising a bone plate including a plurality of fastener holes, the first end of the first and second tips being arranged and configured to engage one of the plurality of fastener holes.

4. The bone reduction system of claim 1, further comprising a bone fastener, the second end of the first and second tips including an enlarged bell housing including an internal cavity arranged and configured to receive a head portion of the bone fastener.

5. The bone reduction system of claim 4, wherein the enlarged bell housing includes a circumferential opening in communication with the internal cavity and a ledge, wherein with the head portion of the bone fastener received within the internal cavity, the ledge engages an underside of the head portion of the bone fastener.

6. The bone reduction system of claim 1, wherein moving the first and second handles toward each other causes the first and second arms to move towards each other.

7. The bone reduction system of claim 1, wherein the bone reduction instrument further comprises a locking or tightening mechanism including an externally threaded rod coupled to one of the first and second handles, the externally threaded rod passing through the other one of the first and second handles, and an internally threaded nut arranged and configured to engage the externally threaded rod.

8. The bone reduction system of claim 7, wherein the bone reduction instrument further comprises a force sensor arranged and configured to measure an amount of force being applied to the first and second handles.

9. The bone reduction system of claim 8, wherein the force sensor comprises:
    an outer body including an internally threaded bore arranged and configured to threadably engage the externally threaded rod; and
    a load sensor positioned at an end thereof so that, in use, rotation of the internally threaded nut rotates at least a portion of the force sensor into contact with one of the first and second handles.

10. The bone reduction system of claim 9, wherein the force sensor further includes one or more springs positioned within the outer body of the force sensor, in use, rotation of the internally threaded nut causes compression of the one or more springs to provide haptic feedback to a user.

11. The bone reduction system of claim 8, wherein the force sensor further comprises indicia on an outer surface thereof to provide visual feedback to a user.

12. The bone reduction system of claim 11, wherein the indicia includes a plurality of color-coded bands to indicate a level of compression being applied across a bone fracture.

13. A bone reduction system for manipulating one or more patient's bone fragments, the bone reduction system comprising:
    a bone plate including a plurality of fastener holes;
    a plurality of bone fasteners including a first fastener for coupling the bone plate to a first bone fragment and a second fastener for coupling to a second bone fragment;

a bone reduction instrument including a first handle pivotably coupled to a second handle, the first handle including a first arm, the second handle including a second arm, each of the first and second arms including a coupling mechanism; and a first tip selectively coupled to the coupling mechanism of the first arm, and a second tip selectively coupled to the coupling mechanism of the second arm, wherein each of the first and second tips include:
a first end arranged and configured to mate with one of the plurality of fastener holes formed in the bone plate;
a second end arranged and configured to receive a head portion of the second fastener; and
an intermediate portion arranged and configured to couple to the coupling mechanism of the first and second arms.

14. The bone reduction system of claim 13, wherein the coupling mechanism formed in the first and second arms comprises an internally threaded borehole and the intermediate portion of the first and second tips include external threads for threadably engaging the internally threaded borehole formed in the first and second arms.

15. The bone reduction system of claim 13, wherein the second end of the first and second tips includes an enlarged bell housing including an internal cavity arranged and configured to receive the head portion of the second fastener.

16. The bone reduction system of claim 13, wherein the bone reduction instrument further comprises a locking or tightening mechanism including an externally threaded rod coupled to one of the first and second handles, the externally threaded rod passing through the other one of the first and second handles, and an internally threaded nut arranged and configured to engage the externally threaded rod.

17. The bone reduction system of claim 16, wherein the bone reduction instrument further comprises a force sensor arranged and configured to measure an amount of force being applied to the first and second handles.

18. The bone reduction system of claim 17, wherein the force sensor comprises:
an outer body including an internally threaded bore arranged and configured to threadably engage the externally threaded rod; and
a load sensor positioned at an end thereof so that, in use, rotation of the internally threaded nut rotates at least a portion of the force sensor into contact with one of the first and second handles.

19. The bone reduction system of claim 18, wherein the force sensor further includes one or more springs positioned within the outer body of the force sensor, in use, rotation of the internally threaded nut causes compression of the one or more springs to provide haptic feedback to a user.

20. The bone reduction system of claim 18, wherein the force sensor further comprises indicia on an outer surface thereof to provide visual feedback to a user.

21. The bone reduction system of claim 20, wherein the indicia includes a plurality of color-coded bands to indicate a level of compression being applied across a bone fracture.

22. A method for reducing a bone fracture, the method comprising:
coupling a bone plate to a first bone fragment of a patient's bone;
implanting a bone fastener into a second bone fragment of the patient's bone;
coupling a bone reduction instrument to the bone plate and the bone fastener, wherein the bone reduction instrument includes interchangeable first and second tips, each of the first and second tips including a first end to couple with a fastener hole formed in the bone plate, a second end to receive a head portion of the bone fastener, and an intermediate portion arranged and configured to couple to the bone reduction instrument; and
compressing first and second handles of the bone reduction instrument to compress the bone fracture positioned between the first and second bone fragments;
wherein the bone reduction instrument is arranged and configured to decouple from the bone fastener and the bone plate without requiring the bone fastener to be removed from the second bone fragment.

23. The method of claim 22, wherein the first handle is pivotably coupled to the second handle, the first handle includes a first arm, the second handle includes a second arm, and each of the first and second arms includes a coupling mechanism arranged and configured to engage one of the first and second tips.

24. The method of claim 23, wherein the coupling mechanism formed in the first and second arms comprises an internally threaded borehole and the intermediate portion of the first and second tips include external threads for threadably engaging the internally threaded borehole formed in the first and second arms.

25. The method of claim 22, further comprising measuring a force applied across the bone fracture; and
determining whether the force falls within a predetermined acceptable range.

* * * * *